(12) United States Patent
Parnagian

(10) Patent No.: US 8,517,939 B2
(45) Date of Patent: Aug. 27, 2013

(54) MEDICAL INSTRUMENT WITH LOW POWER, HIGH CONTRAST DISPLAY

(75) Inventor: Edward C. Parnagian, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 1905 days.

(21) Appl. No.: 10/544,407

(22) PCT Filed: Jun. 6, 2005

(86) PCT No.: PCT/IB2005/051836
§ 371 (c)(1),
(2), (4) Date: Aug. 3, 2005

(87) PCT Pub. No.: WO2006/000926
PCT Pub. Date: Jan. 5, 2006

(65) Prior Publication Data
US 2007/0270669 A1    Nov. 22, 2007

Related U.S. Application Data

(60) Provisional application No. 60/582,613, filed on Jun. 24, 2004.

(51) Int. Cl.
*A61B 5/00* (2006.01)
(52) U.S. Cl.
USPC .......................... 600/301; 600/300; 128/920
(58) Field of Classification Search
USPC ................ 600/300, 301; 128/903–905, 920
See application file for complete search history.

(56) References Cited

U.S. PATENT DOCUMENTS

| 4,088,992 | A | | 5/1978 | Kmetz et al. | |
|---|---|---|---|---|---|
| 5,464,428 | A | * | 11/1995 | Hill | 607/1 |
| 5,829,878 | A | | 11/1998 | Weiss et al. | |
| 5,876,351 | A | | 3/1999 | Rohde | |
| 5,891,049 | A | * | 4/1999 | Cyrus et al. | 600/523 |
| 5,987,345 | A | * | 11/1999 | Engelmann et al. | 600/407 |

(Continued)

FOREIGN PATENT DOCUMENTS

| EP | 0 935 156 A | 8/1999 |
|---|---|---|
| EP | 0935156 A1 | 8/1999 |

(Continued)

OTHER PUBLICATIONS

Zoll Medical Corporation, "Zoll Launches E Series Defibrillator Designed for EMS Professionals," Press Release, Jul. 26, 2005, Chelmsford, MA, http://www.zoll.com/PressRelease.asp?nPressReleaseID=157.

(Continued)

*Primary Examiner* — Sam Yao

(57) ABSTRACT

A patient monitoring/defibrillation instrument displays patient vital signs in numeric form or as graphical waveform traces. Under normal room lighting conditions the numeric and waveform information is displayed in color against a black or gray background. When the patient monitor is operated outside or in bright light, the user has the option to select a color map for display of the patient vital signs information in a highly contrasting manner such as black numeric or waveform information against a bright background such as yellow. The high contrast display, while being objectionable in most indoor settings, has been found to comfortably and effectively display the monitored information in sunlight without the need to increase power to the display.

23 Claims, 5 Drawing Sheets

(56) References Cited

U.S. PATENT DOCUMENTS

| | | | |
|---|---|---|---|
| 6,496,177 B1 * | 12/2002 | Burton | 345/101 |
| 6,507,380 B1 | 1/2003 | Iijima | |
| 6,561,979 B1 | 5/2003 | Wood et al. | |
| 2002/0105508 A1 | 8/2002 | Inada | |
| 2005/0037815 A1 * | 2/2005 | Besharat et al. | 455/566 |
| 2005/0159139 A1 * | 7/2005 | Benco et al. | 455/414.1 |
| 2005/0212824 A1 * | 9/2005 | Marcinkiewicz et al. | 345/690 |

FOREIGN PATENT DOCUMENTS

| | | |
|---|---|---|
| WO | 98/16806 A1 | 4/1998 |
| WO | 99/05562 A1 | 4/1999 |
| WO | WO 2006/000926 A1 | 1/2006 |

OTHER PUBLICATIONS

Zoll Medical Corporation, "There is No Such Thing as Too Tough," Sales Brochure, 2005, 01824-4105.

* cited by examiner

MEDICAL INSTRUMENT WITH LOW POWER, HIGH CONTRAST DISPLAY

CROSS REFERENCE TO RELATED APPLICATION

This application claims the benefit of U.S. provisional application serial no. 60/582,613 filed Jun. 24, 2004, which is incorporated herein by reference.

This invention relates to medical instruments and, in particular, to patient monitoring and resuscitation instruments for use in a variety of ambient lighting conditions.

Patient monitors and defibrillators are in widespread use in hospitals and by emergency medical personnel for monitoring the vital signs of patients and responding thereto as, for instance, by defibrillating ventricular fibrillation. In the past these monitors have been of substantial size and weight and employed a cathode ray tube monitor to display patient vital signs such as heartbeat, respiration, blood oxygen, and other parameters of bodily functions. Today these monitors are becoming smaller and lighter and, in many instances, are designed for portability. This portability enables the monitors to be used in their conventional settings in emergency rooms and intensive care units, and also enables them to be hung on a bedrail as a patient is moved from one location in a hospital to another. It also enables the monitors and defibrillators to be used in ambulances and other emergency vehicles, and even to be used at the site of an accident or other medical emergency. Such a portable instrument can even be placed in use out-of-doors, enabling emergency personnel to immediately begin monitoring a patient's vital signs and administering life-saving treatments afforded by the instrument.

Patient monitors and defibrillators typically include a display in which the aforementioned patient vital signs are graphically and numerically displayed. The portability of the instrument can mean that the display must be viewed in a wide range of ambient lighting conditions. For example, the instrument may at times be used in a dimly lighted lab or clinic where ambient lighting is kept low to optimally view the images on diagnostic imaging equipment. At other times a portable instrument may be used in bright sunlight. Regardless of the ambient lighting conditions the monitor display must be easy to view against brightly or dimly lighted backgrounds. In sunlight, where the ambient light reduces the contrast and apparent brightness of the display, the immediate inclination of a user is to turn up the display brightness or contrast. However, such higher display drive levels can require more power and decrease the operating time of the battery-powered instrument. Accordingly it is desirable to enable the display to be viewed under varying lighting conditions but without resorting to a mode of operation which will excessively reduce the battery operating time.

In accordance with the principles of the present invention, a patient monitor/defibrillator is provided with a display that will selectively increase the contrast of displayed numerical and graphical information without excessively reducing battery life. This is provided by a display which displays brightly colored numbers and traces against a dark background in dimly lighted or normal room lighted environments. When the monitor is used is sunlight or in brightly lighted conditions, the display pixels are remapped to display dark numbers and traces against a bright background. While such a remapping of the display would seem out-of-place—and actually uncomfortable—at normal indoor light levels, the remapping provides an acceptable display contrast under brightly lighted conditions. The remapping can avoid the need to compensate for bright ambient lighting by significantly increasing the power supplied to the display. In an illustrated embodiment, the display is remapped from colored numbers and traces against a black or gray background to black traces and numbers against a yellow background, affording a contrast improvement in bright daylight operation without adjustment of the brightness or contrast control of the display.

Figure 4A:
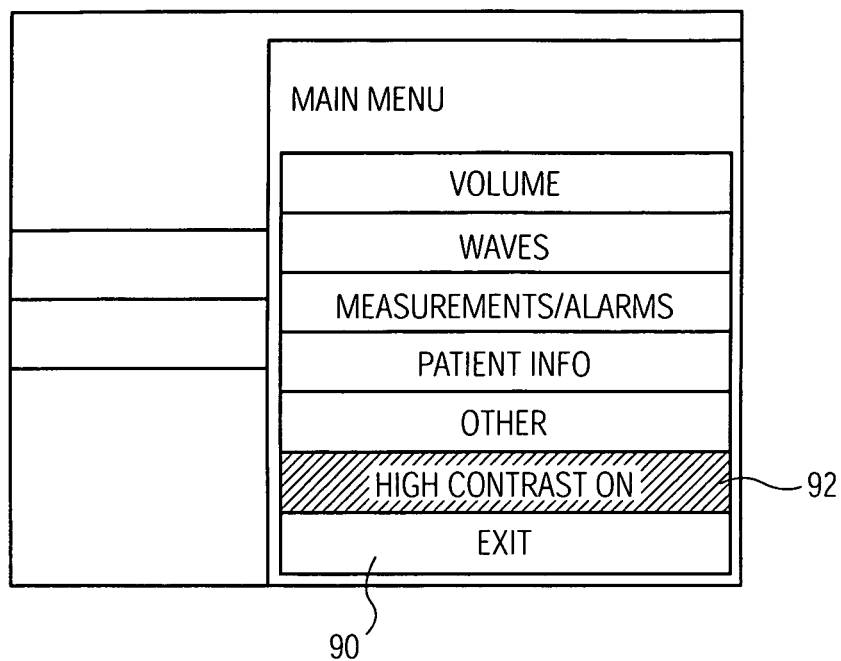
Figure 4B:
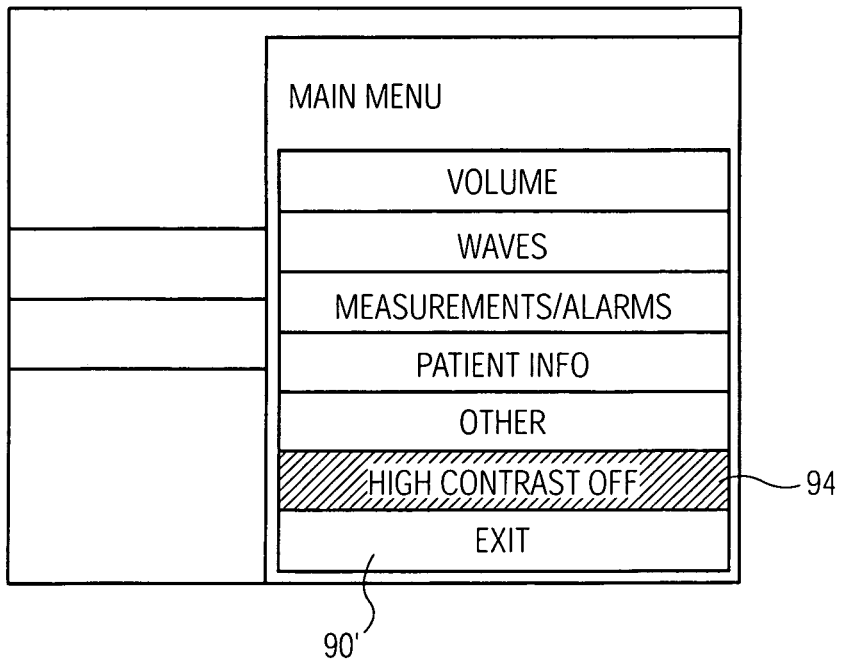

FIGS. 4*a* and 4*b* illustrate the menu of a patient monitor/defibrillator constructed in accordance with the principles of the present invention showing the selection of normal and high contrast operating modes.

Figure 5:
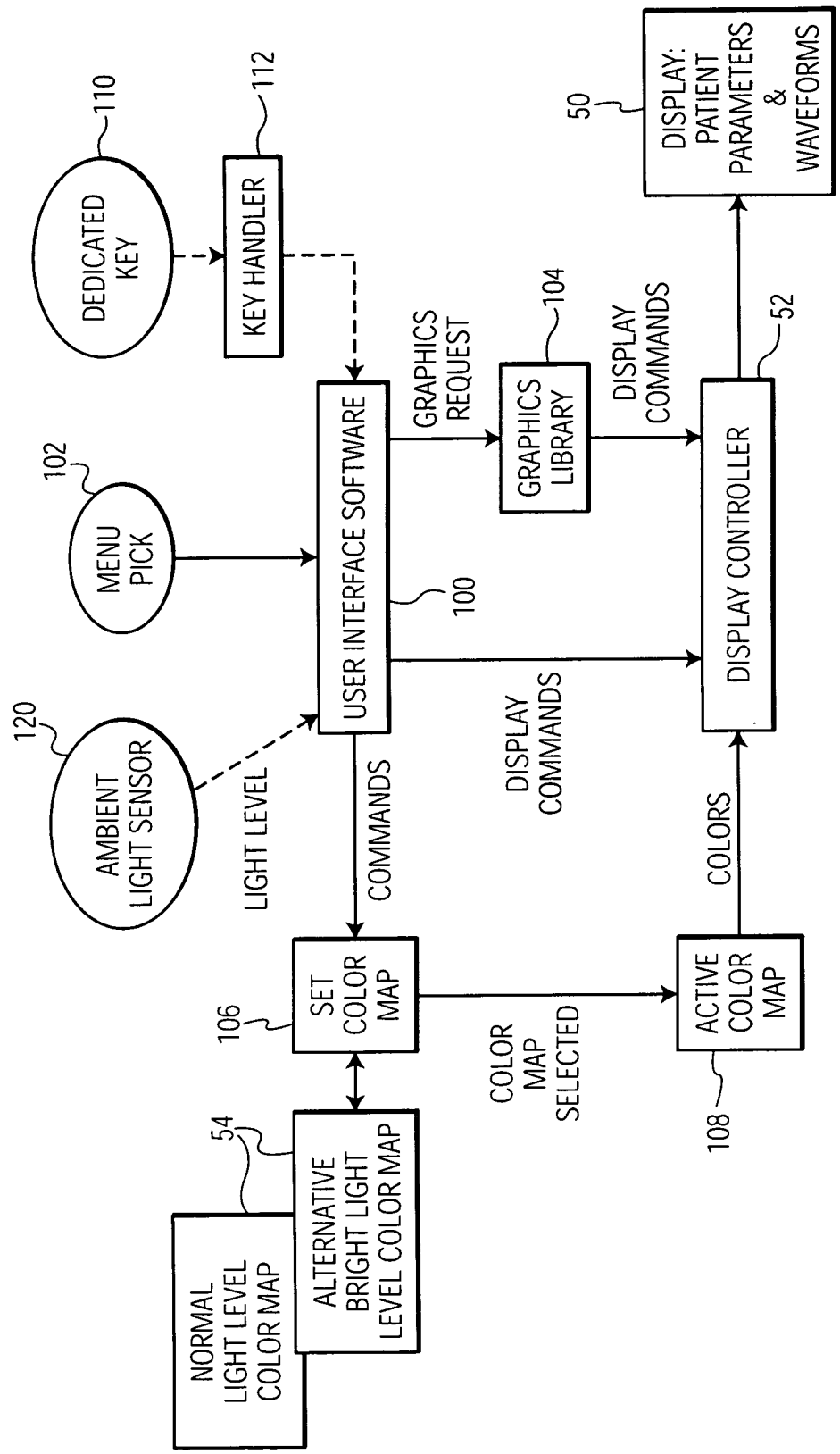

FIG. 5 illustrates in block diagram form a process for switching between normal and high contrast operating modes in response to the menu settings of FIG. 4A and 4B.

Figure 1:
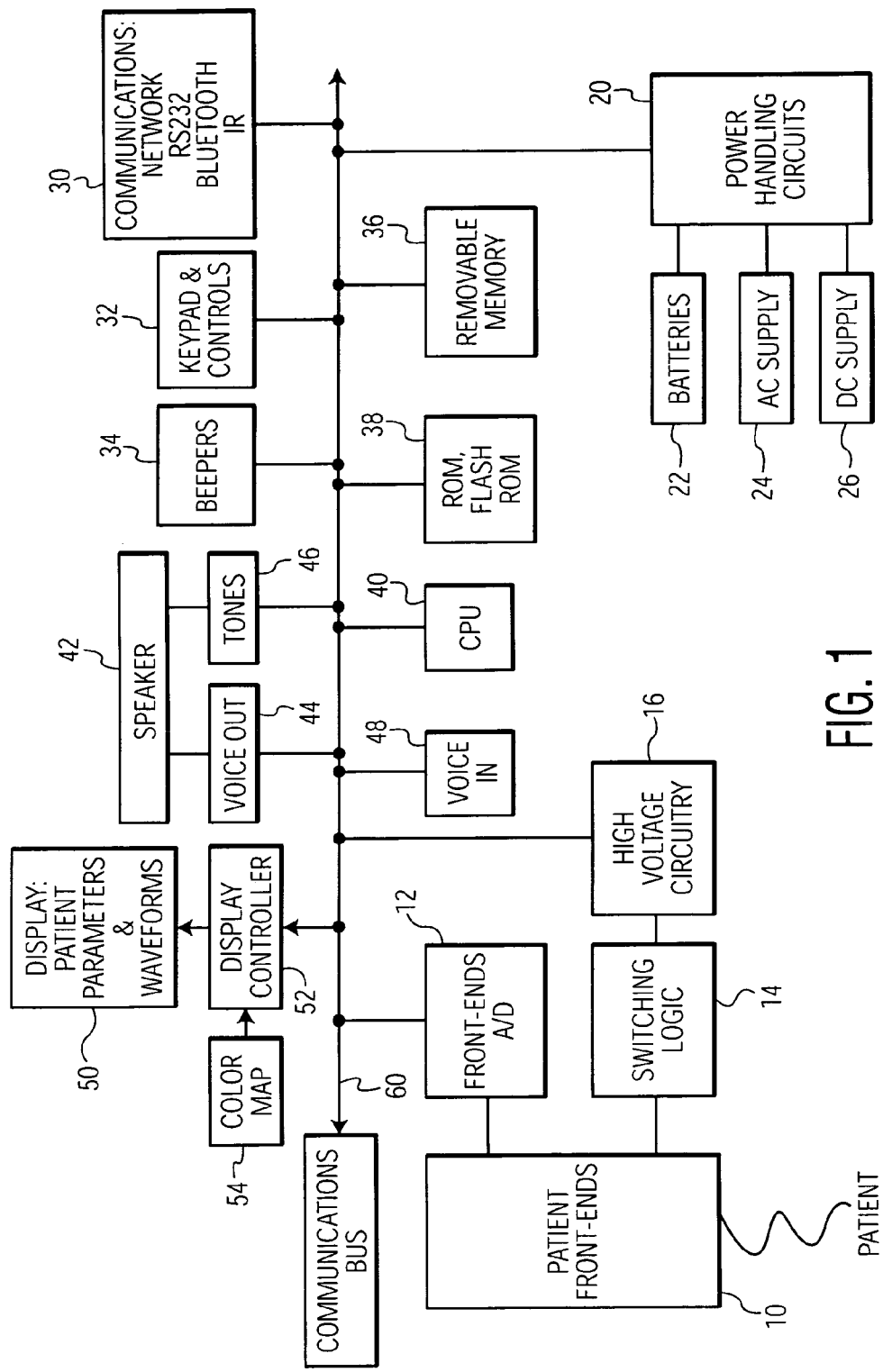
FIG. 1 illustrates in block diagram form a portable patient monitor/defibrillator constructed in accordance with the principles of the present invention.

Referring first to FIG. 1, a patient monitor/defibrillator constructed in accordance with the principles of the present invention is shown in block diagram form. The instrument shown in FIG. 1 is capable of performing defibrillation of a patient who is experiencing ventricular fibrillation. It is also capable of performing ECG monitoring including the cardiac monitoring necessary for automatic defibrillation decision-making. The illustrated monitor is also capable of $SpO_2$ oxygen sensing, noninvasive blood pressure monitoring, and end tidal $CO_2$ monitoring. Other functions such as invasive blood pressure monitoring and patient temperature monitoring may also be found in such a multi-functional instrument. The monitor has a plurality of patient front-ends, which are input circuitry for the sensors attached to the patient. This circuitry includes conventional sensing and amplification circuitry for ECG electrodes, for optical oxygen sensors, for pressure sensing and for carbon dioxide sensing, among others. The information received by the patient sensors and processed by the front-end circuitry 10 is digitized by front-end A/D converters 12. The digitized information is coupled to processing circuitry of the instrument by a communications bus 60 which connects data between the various modules of the instrument.

The instrument includes high voltage circuitry 16 for defibrillator operation. The high voltage circuitry produces the high voltage pulse necessary for defibrillation which is connected at the appropriate time by switching logic 14 to defibrillator electrodes coupled to the patient. This circuitry provides the high voltage shock needed to disrupt the ventricular fibrillation and returns the heart to a normal rhythm. The shock level and waveform delivered for defibrillation can be automatically calculated by a processor in the monitor or can be manually set by an experienced medical technician or physician.

Power for the modules within the instrument is distributed by power handling circuits 20. The power handling circuits 20 will distribute power from batteries 22, from an AC supply 24, or from a DC supply 26. The AC and DC supplies are also coupled to circuitry which charges the batteries when the monitor is powered from these external power sources.

The information obtained by the instrument may be sent to other instruments or locations by communications circuitry 30. This may include a network connection, an RS232 connection, or a wireless connection (e.g. Bluetooth, WiFi or infrared, etc.).

The instrument is operated and adjusted by means of a keypad and controls 32. In a constructed embodiment the keypad is a membrane keypad providing integrity against environmental conditions. Controls such as an on/off switch, power level and shock delivery controls for defibrillation, a printer, and other functions may also be provided.

The monitor is operated under control of a central processing unit (CPU) 40. The CPU runs software stored on a read-only memory (ROM) 38. Flash ROM is also provided for the control of feature setups and new or special capabilities such as waveform information. Removable memory 36 is provided for storage of information generated during a patient episode such a ventricular fibrillation. Patient information such as cardiac waveforms before and after defibrillation are also stored on the removable memory 36, which can be removed and given to a subsequent care-giver for review, record-keeping, and subsequent diagnosis. The removable memory 36 could also record voice information from a care-giver speaking into a microphone 48.

Beepers 34 are used to drive a solid-state sound source that produces short "chirping" sounds. These sounds indicate that the instrument's resident self-test has detected a low battery level or a malfunction in a patient-critical circuit group. There is also a dedicated display on the front of the instrument that presents a large, flashing, red X to indicate a low battery level or a large, fixed, red X to identify a circuit failure.

Tones 46 are produced by the software and then used to drive the speaker 42. This capability is used during certain monitoring functions such as a short tone in response to each heart cycle. Combinations of tones are used to issue audible alerts and alarms when a patient's vital measurements fall outside the alarm limits selected.

The speaker 42 can reproduce pre-recorded voice instructions and information stored and reproduced from voice out circuitry 44.

In accordance with the principles of the present invention a display 50 is provided for the display of patient parameters and waveforms as discussed more particularly below. The information to be displayed is provided to a display controller 52 which provides the necessary drive signals for display of the information on the display. In a constructed embodiment the display is a color LCD display, although other types of display such as a CRT display may be used in a particular embodiment. The display controller 52 displays information in accordance with a color map provided by color map store 54. In a constructed embodiment the color map is stored in tabular form. In other embodiments the color map may be stored as an algorithm or other programmed information. In the constructed embodiment the display information is coupled to the display with a color code by which the display controller selects the pixels for display of the desired information and background colors, as explained more fully below.

Figure 2:
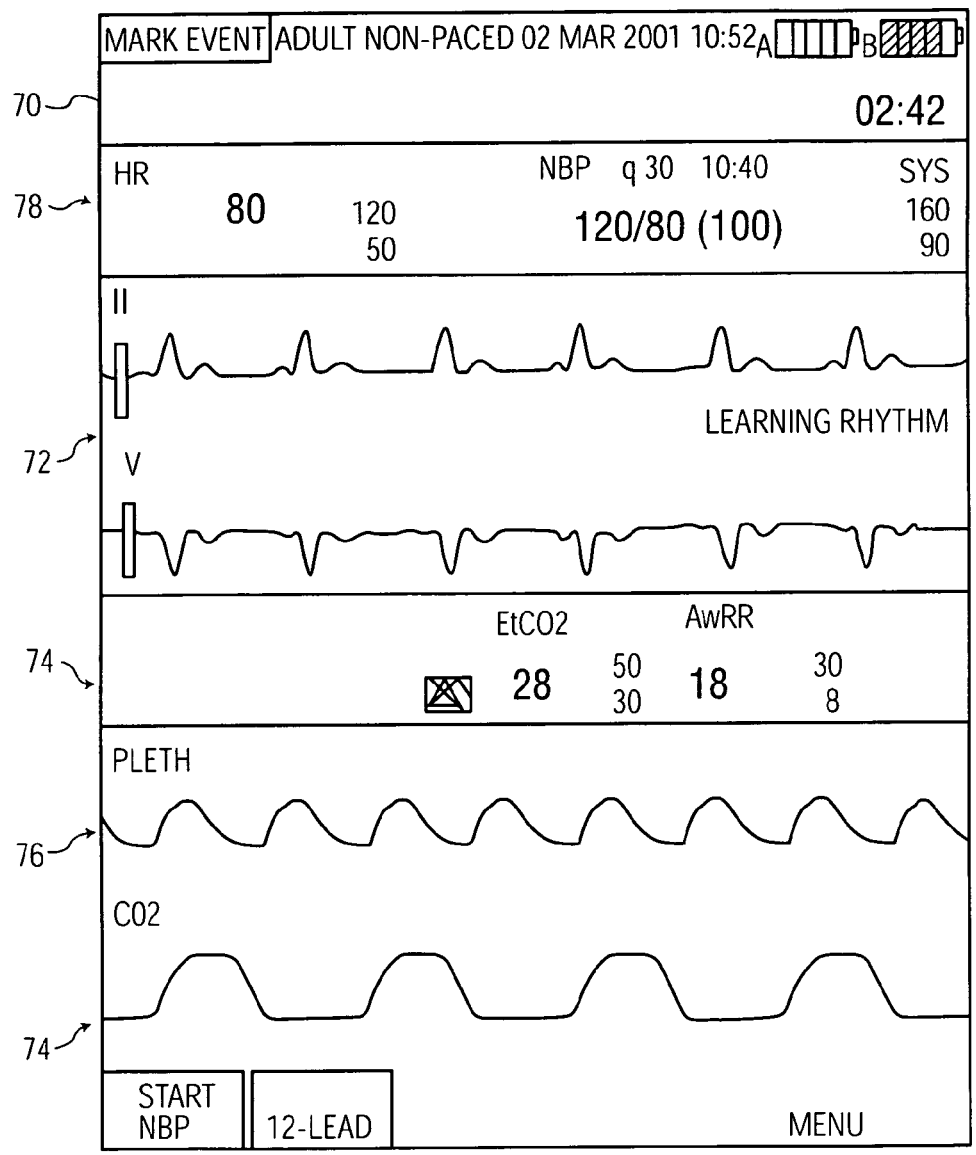
FIG. 2 illustrates a patient monitor/defibrillator display of the present invention with colored numbers and traces against black and gray backgrounds for room lighted operating conditions.

FIG. 2 illustrates the display 70 of a monitor constructed in accordance with the principles of the present invention during normal operation as might be found inside a hospital. Under such room light conditions the background of the display 70 is black, or gray as indicated by reference numeral 78. The graphical information at the very top of the display 70 is displayed in which against the black background. To readily distinguish and associate the different types of information displayed, the numerical and graphical information is displayed in color. For instance the numerical heart rate 80 and the heart traces below as indicated at 72 are displayed in green. The numerical $CO_2$ reading of 28 and the $CO_2$ trace indicated at 74 are displayed in light blue. The plethysmograph trace 76 is displayed in purple. Such a color display against a black or gray background has been found to be pleasing to view in an indoors environment where ambient light conditions are not high.

Figure 3:
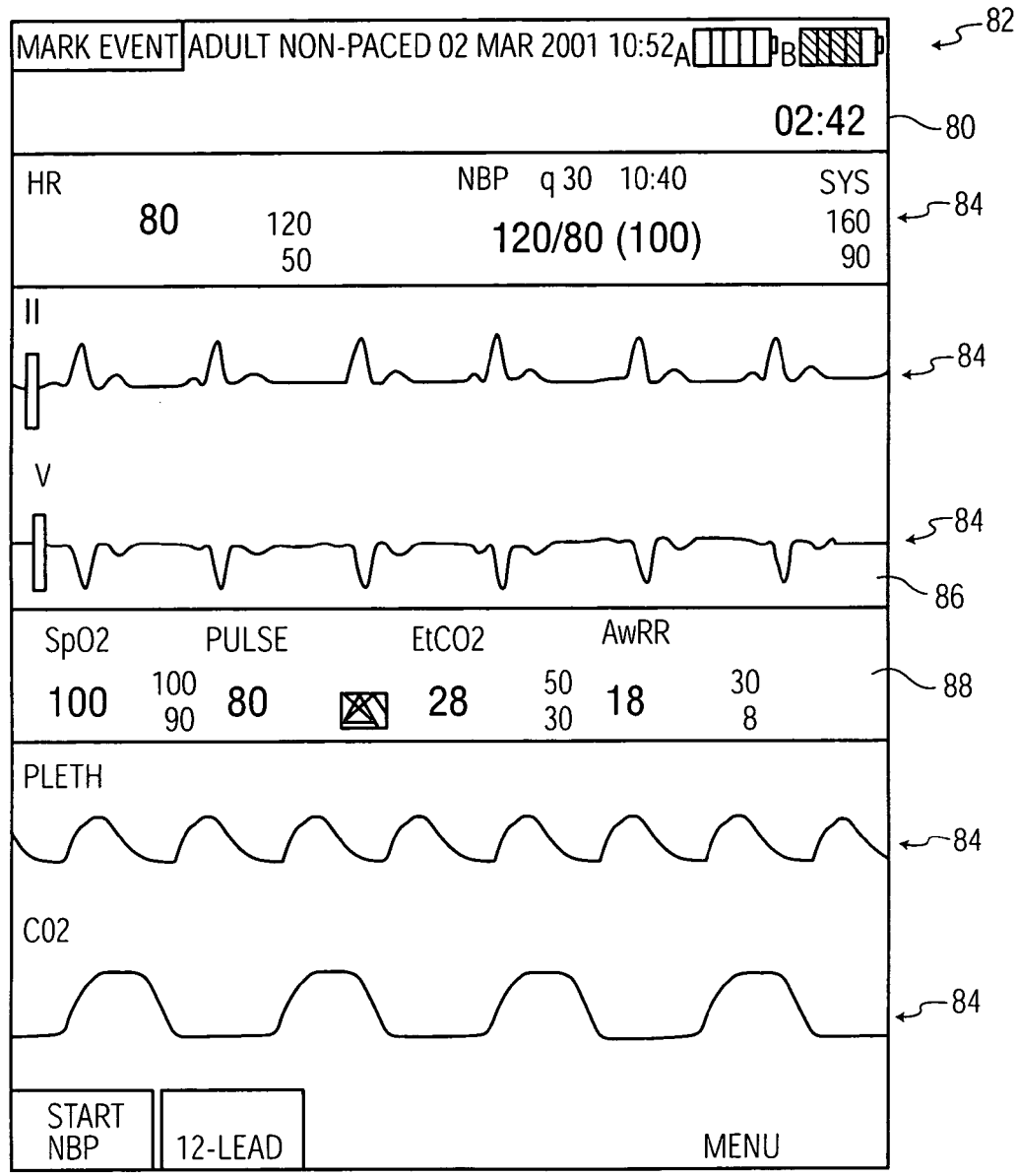
FIG. 3 illustrates the patient monitor/defibrillator display of FIG. 2 when remapped for outdoor display of black numbers and traces against a yellow background.

FIG. 3 illustrates the information of FIG. 2 when displayed in a high contrast display 80 for brightly lighted or sunlight conditions in accordance with the present invention. In FIG. 3 the display colors have all been remapped so that the background color 86 is yellow instead of black. In the illustrated embodiment some of the rows of information such as that indicated at 88 are contrasted from other rows by being offset by a slightly grayed yellow color. The graphical information 82 at the top of the display and the traces and numbers in other areas of the display are all displayed in black. While this display appearance might be irritating and seem out of place indoors, it has been found to convey a satisfactory and highly contrasted and readable display in sunlight and brightly lighted conditions. Other contrasting color combinations such as dark gray or green against an orange or white background may also be suitable for the high contrast display 80.

FIGS. 4a and 4b illustrate the selection of the normal and high contrast viewing modes in a constructed embodiment of the present invention. The user depresses a "Menu" button on the keypad which displays a pop-up menu 90 as shown in FIG. 4a. The user then depresses the "up" or "down" arrow buttons to highlight the "High Contrast On" menu row 92 in FIG. 4a. When the "Enter" button is depressed, the menu disappears, and the display is remapped to the high contrast mode shown in FIG. 3. When the user desires to return to the normal display mode the "Menu" button is depressed again, the arrow buttons are used if necessary to highlight the "High Contrast Off" menu row 94 as shown in FIG. 4b. When the "Enter" button is depressed, the menu disappears and the display is remapped to the conventional format shown in FIG. 2.

FIG. 5 illustrates in greater detail a process for changing the display mode. The user selects the new display mode as shown by menu pick 102. The user interface software 100 responds to this selection by setting a new color map 106 from the normal light level and bright light level color maps stored in the color map store 54. A new graphics request is issued to a graphics library 104 which provides new display commands for the new color map to the display controller 52. The newly selected color map is loaded into the active color map buffer 108, making the colors of the new map available to the display controller. The display controller then commands the display 50 to display the currently displayed information in accordance with the new color map.

FIG. 5 illustrates two other alternative implementations of the present invention. Instead of selecting the display map from a pop-up menu as shown in FIGS. 4a and 4b, the keypad may have a dedicated key 110 for changing the display contrast. Each time the user depresses the dedicated key, a key handler 112 responds by toggling the display to the other display mode. Another alternative is to have an ambient light sensor 120 on the instrument which senses the ambient light level in which the monitor is operating. The user interface software responds to a change in light level above or below a preset or user adjustable threshold or thresholds by changing the display automatically. In a constructed embodiment the user may be given a choice of automatic or manual selection of the display mode.

While the above embodiments have illustrated the use of color maps for the display, it will be appreciated that a monochrome display may also be set for normal and high contrast display by adjustment and switching of the display luminance levels.

What is claimed is:

1. A monitor/defibrillator instrument which may be operated in different ambient lighting conditions comprising:
   high voltage circuitry which produces a high voltage defibrillation pulse;
   circuitry which produces a measure of one or more patient bodily functions;
   a display, coupled to the circuitry, which displays the bodily function measure in numeric or graphical form;
   a display, coupled to the circuitry, which displays the bodily function measure in numeric or graphical form;
   a display map storage device which stores a first display map which causes the display of a bright bodily function measure against a dark background when selected during use of the monitoring instrument in an indoor setting of relatively low ambient light and a second display map which causes the display of a dark bodily function measure against a bright background when selected during use of the monitoring instrument in an outdoor setting of relatively high ambient light;
   a user control by which a user selects one of the display maps; and
   a display controller, coupled to the display and responsive to the user control, for setting the display to display the bodily function measure in accordance with a selected display map.

2. The monitor/defibrillator instrument of claim 1, wherein one of the display maps acts to cause the display of a colored bodily function measure against a black or gray background, and another of the display maps acts to cause the display of a black or gray bodily function measure against a bright background.

3. The monitor/defibrillator instrument of claim 1, wherein one of the display maps acts to cause the display of a brightly displayed bodily function measure against a black or gray background, and another of the display maps acts to cause the display of a black or gray bodily function measure against a bright background.

4. The monitor/defibrillator instrument of claim 1, wherein the user control comprises a menu pick on the display.

5. The monitor/defibrillator instrument of claim 1, wherein the user control comprises a dedicated button for display contrast control.

6. The monitor/defibrillator instrument of claim 1, further comprising a battery coupled to the display for powering the display.

7. A method for operating a portable patient monitor/defibrillator instrument comprising:
   locating the instrument in an outdoor setting;
   manipulating an operator control to selectively change the display contrast from one which displays numeric or graphical information in a bright color against a dark background to one which displays numeric or graphical information in a dark color against a bright background when the monitoring instrument is used in an outdoor setting,
   wherein selectively changing the display contrast is based on the ambient lighting conditions.

8. The method of claim 7, further comprising:
   locating the instrument in an indoor setting; and
   manipulating the operator control to selectively change the display contrast from one which displays numeric or graphical information in a dark color against a bright background to one which displays numeric or graphical information in a bright color against a dark background.

9. The method of claim 7, wherein the dark color is black.

10. The method of claim 7, wherein manipulating further comprises changing the display contrast to one which display numeric or graphical information in black against a yellow background.

11. A patient monitoring instrument which may be operated in different ambient lighting conditions comprising:
    a display, responsive to bodily function information, which displays cardiac information in numeric and/or graphical form;
    a display controller, coupled to the display, which, in a first mode, causes the display to display the cardiac numeric and/or graphical information as brighter information against a darker background and, in a second mode, causes the display to display the cardiac numeric and/or graphical information as darker information against a brighter background; and
    a user display control, operable by a user and coupled to the display controller, to control the display to show brighter cardiac numeric and/or graphical information against a darker background when the monitoring instrument is used in an indoor setting or as darker information against a brighter background when the monitoring instrument is used in an outdoor setting.

12. The patient monitoring instrument of claim 11, wherein the darker background comprises a black or gray background, and the darker information comprises black numeric and/or graphical information.

13. The patient monitoring instrument of claim 12, wherein the brighter cardiac numeric and/or graphical information comprises a color which includes a yellow color component and the brighter background comprises a color which includes a yellow color component.

14. The patient monitoring instrument of claim 12, wherein the brighter cardiac numeric and/or graphical information comprises a substantially white color and the brighter background comprises a substantially white color.

15. The patient monitoring instrument of claim 11, wherein the patient monitoring instrument further includes a defibrillator, wherein the bodily function information comprises information of a defibrillation patient.

16. The patient monitoring instrument of claim 15, wherein the bodily function information comprises at least one of heart rate information and ECG information.

17. The patient monitoring instrument of claim 16, wherein at least one of the heart rate information and ECG information is displayed on the display in graphical form.

18. The patient monitoring instrument of claim 15, wherein the patient monitoring instrument further includes a memory which acts to store data from a patient defibrillation episode.

19. The patient monitoring instrument of claim 18, wherein the memory acts to store at least some of the bodily function information which is displayed on the display in numeric and/or graphical form.

20. The patient monitoring instrument of claim 15, wherein the patient monitoring instrument further comprises a portable, battery-powered instrument.

21. The patient monitoring instrument of claim 15, wherein the display comprises an LCD display.

22. The patient monitoring instrument of claim 21, wherein the LCD display comprises a color display.

23. The patient monitoring instrument of claim 21, wherein the LCD display comprises a monochrome display.

* * * * *